US010565352B2

(12) United States Patent
Eaton, Jr. et al.

(10) Patent No.: US 10,565,352 B2
(45) Date of Patent: Feb. 18, 2020

(54) LOCATION-BASED MANAGEMENT OF HEALTHCARE ENVIRONMENTS

(71) Applicant: CERNER INNOVATION, INC., Kansas City, KS (US)

(72) Inventors: James D. Eaton, Jr., Gardner, KS (US); David L. Compton, Lenexa, KS (US); Justin Nelson, Merriam, KS (US); Paul Cannon, Kansas City, MO (US); Mark Nolte, Lee's Summit, MO (US)

(73) Assignee: Cerner Innovation, Inc., Kansas City, KS (US)

( * ) Notice: Subject to any disclaimer, the term of this patent is extended or adjusted under 35 U.S.C. 154(b) by 0 days.

(21) Appl. No.: 14/139,546

(22) Filed: Dec. 23, 2013

(65) Prior Publication Data

US 2014/0114688 A1    Apr. 24, 2014

Related U.S. Application Data

(62) Division of application No. 12/612,434, filed on Nov. 4, 2009, now Pat. No. 8,700,423.

(51) Int. Cl.
*G16H 40/67* (2018.01)
*G06F 19/00* (2018.01)
(Continued)

(52) U.S. Cl.
CPC ....... *G06F 19/3418* (2013.01); *G06Q 10/087* (2013.01); *G06Q 50/22* (2013.01);
(Continued)

(58) Field of Classification Search
CPC .... A61B 2019/5251; A61B 2019/5272; A61B 5/002; A61B 5/1115; G06Q 50/22;
(Continued)

(56) References Cited

U.S. PATENT DOCUMENTS

| 7,248,933 | B2 * | 7/2007 | Wildman | G06F 19/327 |
| | | | | 700/115 |
| 8,725,526 | B2 * | 5/2014 | Cobbs | G06F 19/327 |
| | | | | 705/2 |

(Continued)

OTHER PUBLICATIONS

Pre-Interview Communication dated May 2, 2014 in U.S. Appl. No. 14/139,537, 5 pages.
(Continued)

*Primary Examiner* — Joseph D Burgess
(74) *Attorney, Agent, or Firm* — Shook, Hardy & Bacon LLP

(57) ABSTRACT

Systems, methods, and computer-readable media for managing healthcare environments are provided. In embodiments, a real-time status of a clinical device, along with a location, is received. The location of the clinical device is obtained via a clinical device identifier that is tracked by a plurality of sensors in a healthcare environment. A clinical device may be identified as inappropriate for use and an alert presented to a clinician including the problem of the clinical device and the location thereof. A replacement clinical device may be located, using clinical identifiers, and presented to the clinician. Such monitoring and location awareness facilitates efficient responses to healthcare situations.

13 Claims, 10 Drawing Sheets

(51) Int. Cl.
*G16H 40/20* (2018.01)
*G16H 10/60* (2018.01)
*G06Q 10/08* (2012.01)
*G06Q 50/22* (2018.01)

(52) U.S. Cl.
CPC ............ *G16H 10/60* (2018.01); *G16H 40/20* (2018.01); *G16H 40/67* (2018.01)

(58) Field of Classification Search
CPC ... G06Q 50/24; G06F 19/327; G06F 19/3418; G06F 19/00; G06F 19/325; G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 40/00; G16H 40/20; G16H 40/40; G16H 40/60; G16H 40/63; G16H 40/67; G16H 50/00; G16H 70/00; G16H 70/20; G16H 70/40; G16H 70/60; G16H 80/00; G16H 50/20; G16H 50/70; G16H 50/30
USPC .......................................... 705/2–3; 340/539
See application file for complete search history.

(56) References Cited

U.S. PATENT DOCUMENTS

| | | | |
|---|---|---|---|
| 9,122,373 B1* | 9/2015 | Nacey | G06F 3/0484 |
| 2003/0074222 A1* | 4/2003 | Rosow et al. | 705/2 |
| 2004/0130446 A1* | 7/2004 | Chen | G08B 25/016 |
| | | | 340/539.12 |
| 2005/0283382 A1 | 12/2005 | Donoghue et al. | |
| 2006/0004605 A1 | 1/2006 | Donoghue et al. | |
| 2006/0049936 A1* | 3/2006 | Collins, Jr. | A61B 5/1115 |
| | | | 340/539.11 |
| 2006/0173710 A1 | 8/2006 | Komischke | |
| 2007/0075862 A1 | 4/2007 | Hunt | |
| 2007/0132597 A1* | 6/2007 | Rodgers | A61B 5/1113 |
| | | | 340/573.1 |
| 2007/0247316 A1 | 10/2007 | Wildman et al. | |
| 2008/0164998 A1 | 7/2008 | Scherpbier et al. | |
| 2009/0037146 A1 | 2/2009 | Trowbridge, Jr. et al. | |
| 2009/0119124 A1 | 5/2009 | Kambaloor | |
| 2009/0231108 A1* | 9/2009 | Caliri | G06Q 10/087 |
| | | | 340/10.5 |
| 2009/0292465 A1 | 11/2009 | Kaldewey et al. | |
| 2010/0114599 A1* | 5/2010 | Lanning | G06Q 50/22 |
| | | | 705/2 |
| 2011/0106561 A1 | 5/2011 | Eaton et al. | |
| 2014/0114681 A1 | 4/2014 | Eaton et al. | |

OTHER PUBLICATIONS

First Action Interview OA dated Jun. 23, 2014 re U.S. Appl. No. 14/139,537, 7 pages.
Final OA dated Nov. 12, 2014, in related U.S. Appl. No. 14/139,537, 16 pp.
Final Office Action dated Oct. 30, 2015 in U.S. Appl. No. 14/139,537, 13 pages.
Non-Final Office Action dated Mar. 21, 2016 in U.S. Appl. No. 14/139,537, 14 pages.
Final Office Action dated Oct. 18, 2016 in U.S. Appl. No. 14/139,537, 16 pages.
Non-Final Office Action dated Mar. 31, 2017 in U.S. Appl. No. 14/139,537, 17 pages.
Final Office Action received for U.S. Appl. No. 12/612,434, dated May 17, 2012, 8 pages.
Final Office Action received for U.S. Appl. No. 14/139,537, dated Dec. 20, 2017, 15 pages.
Non-Final Office Action received for U.S. Appl. No. 12/612,434, dated Dec. 22, 2011, 7 pages.
Non-Final Office Action received for U.S. Appl. No. 14/139,537, dated Feb. 26, 2015, 10 pages.
Notice of Allowance received for U.S. Appl. No. 12/612,434, dated Nov. 29, 2013, 12 pages.
Non-Final Office Action dated May 17, 2018 in U.S. Appl. No. 14/139,537, 10 pages.

* cited by examiner

FIG. 6

LOCATION-BASED MANAGEMENT OF HEALTHCARE ENVIRONMENTS

CROSS-REFERENCE TO RELATED APPLICATIONS

This application is a divisional of, and claims priority from, U.S. patent application Ser. No. 12/612,434, entitled "Location-Based Management of Healthcare Environments," filed Nov. 4, 2009, which is incorporated by reference herein in its entirety.

BACKGROUND

In order to provide effective and efficient management of healthcare environments, healthcare institutions are using a variety of healthcare management systems. Such healthcare management systems may monitor the locations of patients and providers. Recent developments in healthcare have caused an increase in the use of electronic health records (EHR's) and electronic storage of a variety of clinical information.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present invention relate to methods in a clinical computing environment for managing healthcare environments. In one embodiment, a set of computer-useable instructions providing a method for managing healthcare environments is illustrated. Initially, a real-time status of a clinical device is received that indicates whether the clinical device is appropriate for use. The status of the clinical device is identified as indicating that the clinical device is not appropriate for use. Upon identifying that the clinical device is not appropriate for use, an alert is presented indicating both that the clinical device is not appropriate for use and a location of the clinical device within a blueprint of a healthcare environment. A location of at least one replacement clinical device is located and presented within the blueprint.

In another embodiment, a set of computer-useable instructions providing a method for managing healthcare environments is illustrated. A healthcare order that is input into a patient's EHR to be completed for the patient is received from a first clinician. The healthcare order is displayed to a first clinician and associated with one or more tangible items required to fulfill the healthcare order. The location of the one or more tangible items required to fulfill the healthcare order is presented to the second clinician. A second clinician is navigated to the one or more tangible items required to fulfill the healthcare order.

In yet another embodiment, a set of computer-useable instructions providing a method for managing healthcare environments is illustrated. Patient clinical information from a patient's electronic health record and a real-time status of the patient are received. Based upon the patient clinical information and the real-time status of the patient, it is determined that an alert is required. The alert is displayed in both an alert area and a blueprint area of a user interface.

Additional objects, advantages, and novel features of the invention will be set forth in part in the description which follows, and in part will become apparent to those skilled in the art upon examination of the following, or may be learned by practice of the invention.

BRIEF DESCRIPTION OF THE DRAWING

The present invention is described in detail below with reference to the attached drawing figures, wherein:

FIG. 6 is an illustrative graphical user interface display of a patient summary area, in accordance with an embodiment of the present invention;

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

Figure 1:
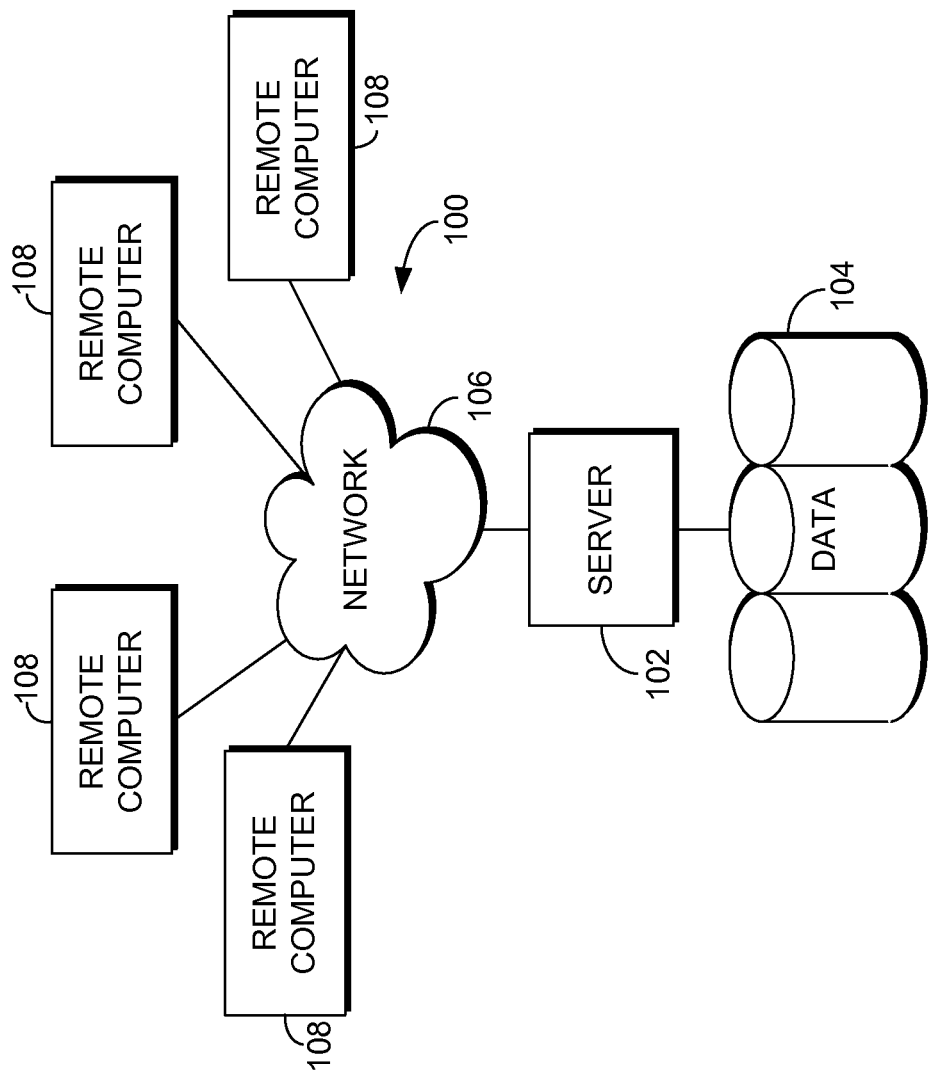
FIG. 1 is a block diagram of an exemplary computing environment suitable for use in implementing the present invention.

Referring to the drawings in general, and initially to FIG. 1 in particular, an exemplary computing system environment, for instance, a medical information computing system, on which embodiments of the present invention may be implemented is illustrated and designated generally as reference numeral 10. It will be understood and appreciated by those of ordinary skill in the art that the illustrated medical information computing system environment 10 is merely an example of one suitable computing environment and is not intended to suggest any limitation as to the scope of use or functionality of the invention. Neither should the medical information computing system environment 10 be interpreted as having any dependency or requirement relating to any single component or combination of components illustrated therein.

Embodiments of the present invention may be operational with numerous other general purpose or special purpose computing system environments or configurations. Examples of well-known computing systems, environments, and/or configurations that may be suitable for use with embodiments of the present invention include, by way of example only, personal computers, server computers, handheld or laptop devices, multiprocessor systems, microprocessor-based systems, set top boxes, programmable consumer electronics, network PCs, minicomputers, mainframe computers, distributed computing environments that include any of the above-mentioned systems or devices, and the like.

Embodiments of the present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 100 includes a general purpose computing device in the form of a control server 102. Components of the control server 102 may include, without limitation, a processing unit, internal system memory, and a suitable system bus for coupling various system components, including database cluster 104, with the server 102. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 102 typically includes, or has access to, a variety of computer readable media, for instance, database cluster 104. Computer readable media can be any available media that may be accessed by server 102, and includes volatile and nonvolatile media, as well as removable and non-removable media. By way of example, and not limitation, computer readable media may include computer storage media and communication media. Computer storage media may include, without limitation, volatile and nonvolatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 102. Communication media typically embodies computer readable instructions, data structures, program modules, or other data in a modulated data signal, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 104, provide storage of computer readable instructions, data structures, program modules, and other data for the server 102.

The server 102 may operate in a computer network 106 using logical connections to one or more remote computers 108. Remote computers 108 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The remote computers 108 may also be physically located in non-traditional medical care environments so that the entire health care community may be capable of integration on the network. The remote computers 108 may be personal computers, servers, routers, network PCs, peer devices, other common network nodes, or the like, and may include some or all of the components described above in relation to the server 102. The devices can be personal digital assistants or other like devices.

Exemplary computer networks 106 may include, without limitation, local area networks (LANs) and/or wide area networks (WANs). Such networking environments are commonplace in offices, enterprise-wide computer networks, intranets, and the Internet. When utilized in a WAN networking environment, the server 102 may include a modem or other means for establishing communications over the WAN, such as the Internet. In a networked environment, program modules or portions thereof may be stored in the server 102, in the database cluster 104, or on any of the remote computers 108. For example, and not by way of limitation, various application programs may reside on the memory associated with any one or more of the remote computers 108. It will be appreciated by those of ordinary skill in the art that the network connections shown are exemplary and other means of establishing a communications link between the computers (e.g., server 102 and remote computers 108) may be utilized.

In operation, a user may enter commands and information into the server 102 or convey the commands and information to the server 102 via one or more of the remote computers 108 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 102. In addition to a monitor, the server 102 and/or remote computers 108 may include other peripheral output devices, such as speakers and a printer.

Although many other internal components of the server 102 and the remote computers 108 are not shown, those of ordinary skill in the art will appreciate that such components and their interconnection are well known. Accordingly, additional details concerning the internal construction of the server 102 and the remote computers 108 are not further disclosed herein.

Although methods and systems of embodiments of the present invention are described as being implemented in a WINDOWS operating system, operating in conjunction with an Internet-based system, one of ordinary skill in the art will recognize that the described methods and systems can be implemented in any system supporting the receipt and processing of healthcare orders. As contemplated by the language above, the methods and systems of embodiments of the present invention may also be implemented on a stand-alone desktop, personal computer, or any other computing device used in a healthcare environment or any of a number of other locations.

As previously mentioned, the present invention is related to managing healthcare environments. More particularly, the present invention is related to location-based management of healthcare environments and resources therein. Clinical integration of a healthcare management system with patients' electronic records would offer the most efficient healthcare management system by tracking healthcare resources such that the system is aware of the location of healthcare resources and may use the location awareness in combination with clinical information stored in an EHR.

Healthcare resources such as clinicians, patients, equipment, clinical devices, and the like may be tracked via a plurality of sensors in the healthcare environment. The sensors in the healthcare environment may utilize ultrasound technology, infrared technology, radio-frequency identification technology, and the like. Using said technology, the sensors send out signals to clinician identifiers, patient identifiers, item identifiers, clinical device identifiers, or the like. An exemplary sensor system is the Cricket Indoor Location System sponsored by the MIT Project Oxygen partnership.

The signals are received by the identifiers and the identifiers respond to the signals. A response from an identifier is received by the sensors and the sensors are able to recognize and determine the location of the responding identifier and, thus, are aware of the resources within the healthcare environment. The respective identifiers associated with the resources may be located, e.g., on the person, on the item, or on the device. Exemplary identifiers include badges, wristbands, tags, and the like. The locations of clinicians, patients, equipment, or the like, associated with a responding identifier, may be presented or displayed on a display of a computing device, such as remote computer 108 of FIG. 1.

The locations of the clinicians, patients, clinical devices, or the like, are useful when locating a desired item and/or individual. Additionally, the location information may be used in combination with clinical information from an electronic health record (EHR) or with an alert presented based on clinical information, location information, clinical device information, or a combination thereof.

Figure 2:
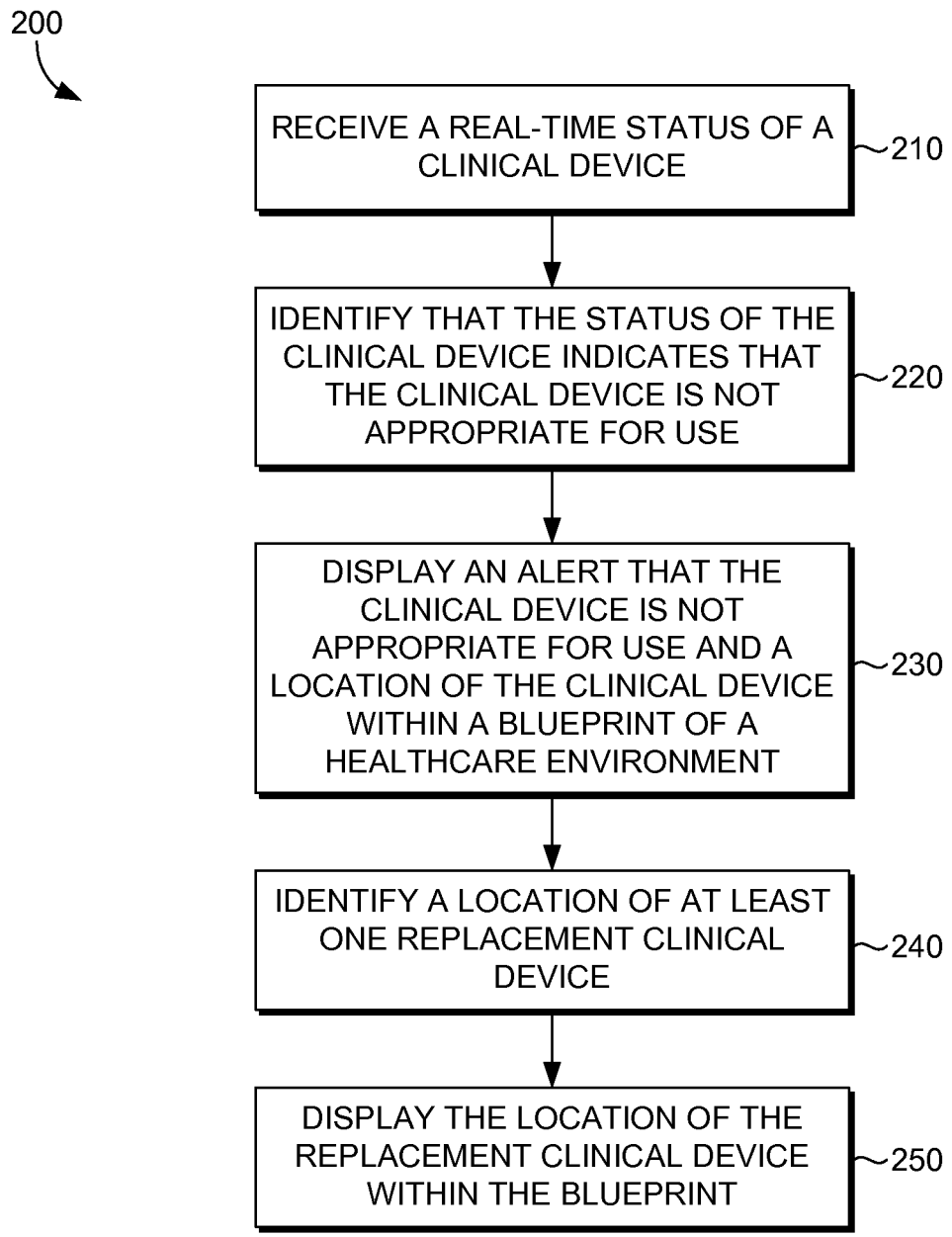
FIG. 2 is a flow diagram illustrating a first exemplary method for managing healthcare environments, in accordance with an embodiment of the present invention.

Alerts may be presented regarding patients, clinical devices, or the like. FIG. 2 represents an exemplary method 200 for managing healthcare environments by generating an alert. Initially, a real-time status of a clinical device is received directly from a clinical device interface at block 210. A real-time status, as used herein, refers to the most recently received status of a clinical device. For example, data output by a clinical device is continuously monitored. Said continuous monitoring provides periodic status updates for the clinical device. The data received most recently is the real-time status of the clinical device.

The real-time status of a clinical device may indicate that the clinical device is appropriate for use or not appropriate for use. More particularly, the status of the clinical device may indicate that the clinical device is in use and functioning, not in use and capable of functioning, in use and requires maintenance, not in use and requires maintenance, in use and not functioning, not in use and not able to function, or the like. An alert for a clinical device may also indicate the name of the clinical device and the problem associated with the clinical device. For instance, an IV pump may be low on fluids and require immediate attention. An alert for that situation may indicate the name of the clinical device (e.g., IV pump) and that the IV pump is low on fluids.

Figure 5:
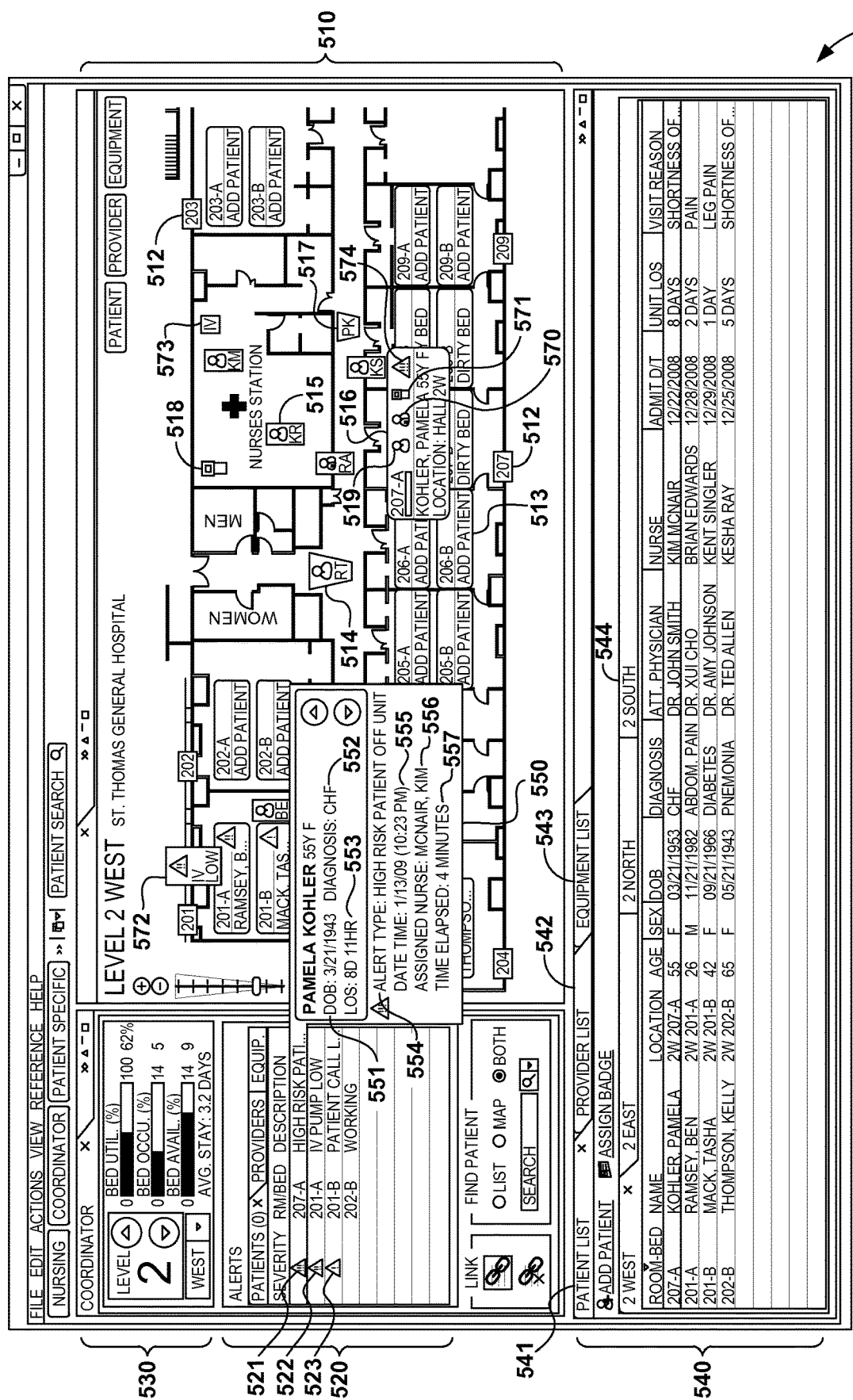
FIG. 5 is an illustrative graphical user interface display of an alert generated for a patient, in accordance with an embodiment of the present invention.

The status of the clinical device is identified as indicating that the clinical device is not appropriate for use at block 220. Upon identifying that the clinical device is not appropriate for use, an alert is presented at block 230. The alert is displayed within a blueprint of a healthcare environment. The blueprint also indicates the location of the clinical device such that a clinician viewing the alert may quickly locate the clinical device, as shown in FIG. 5 and discussed in greater detail below. The alert may be presented to a clinician associated with the patient (e.g., a nurse assigned to the patient), a clinician near the patient in location, or the like.

Clinical device location information is accessed from the plurality of sensors in the healthcare environment. Each clinical device is associated with a clinical device identifier that may be located on a badge, a tag, or any identifying device known in the art to facilitate tracking of items by the plurality of sensors in the healthcare environment utilizing ultrasound technology, infrared technology, radio-frequency identification technology, or the like.

A location of at least one replacement clinical device is identified at block 240. To identify a location of at least one replacement clinical device, a list of available clinical devices is accessed. The list of available clinical devices may include all clinical devices that are currently available in the healthcare environment. In another embodiment, the list may only include available clinical devices that meet the same criteria as the clinical device that requires replacement. An appropriate replacement device is then determined by identifying features of the clinical device requiring replacement and searching the list of available clinical devices to identify available clinical devices with the same features as the clinical device requiring replacement. For example, a pump will be replaced with another pump, a ventilator will be replaced with another ventilator, etc.

Once appropriate replacement clinical devices are identified, the most appropriate replacement clinical device is determined. By way of example only, assume that a ventilator on Floor 3 West needs to be replaced. The list of appropriate replacement clinical devices includes a ventilator on Floor 3 West and a ventilator on Floor 8 East. The most appropriate replacement clinical device may be the ventilator that is closest to the clinical device requiring replacement, i.e., the ventilator on Floor 3 West.

The location of the replacement clinical device is displayed within the blueprint of the healthcare environment at block 250. The replacement clinical device may be determined based on proximity of the replacement clinical device to the clinical device requiring replacement. The replacement clinical device may also be determined based on proximity of the location of the replacement clinical device to the location of the patient. Alternatively, the replacement clinical device may be determined based on proximity of the location of the replacement clinical device to the location of the clinician.

Figure 3:
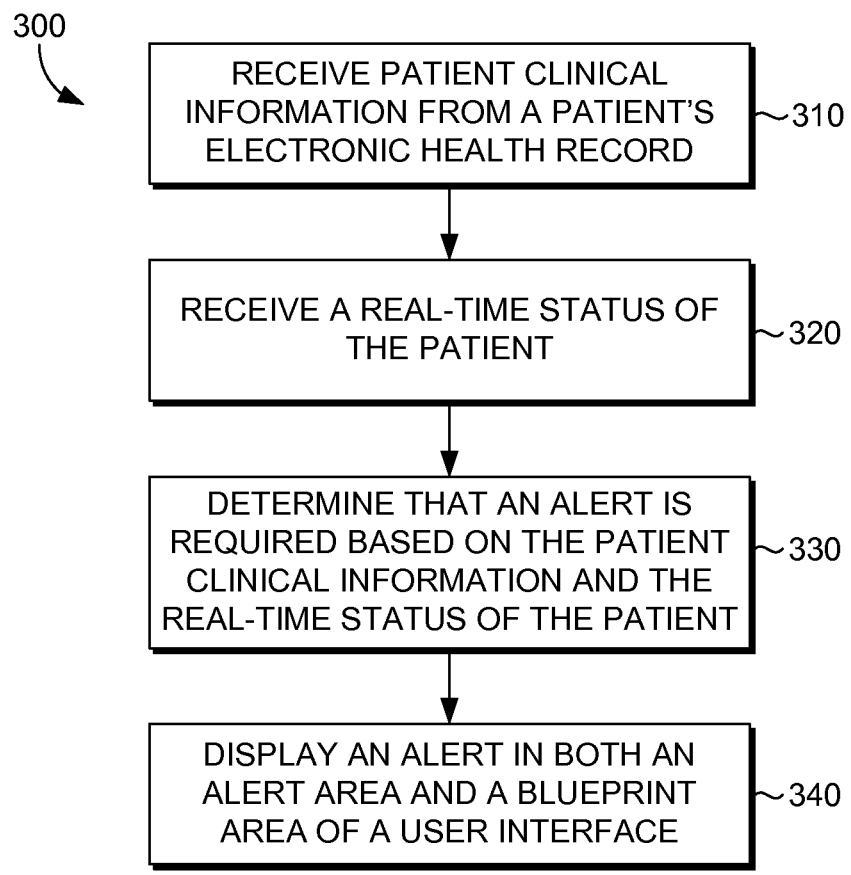
FIG. 3 is a flow diagram illustrating a second exemplary method for managing healthcare environments, in accordance with an embodiment of the present invention.

An exemplary method 300 for managing healthcare environments by generating an alert for a patient is illustrated in FIG. 3. Initially, patient clinical information is received from a patient's EHR at block 310. A real-time status of the patient is received at block 320. Similar to the real-time status of a clinical device, a real-time status of a patient, as used herein, refers to the most recent status update of patient information. The real-time status of the patient may include a location of the patient. Patient location information is based on a patient identifier that is tracked via a plurality of sensors in a healthcare environment. The patient identifier may be located on a wristband, a badge, or any other manner for tracking a patient in a healthcare environment.

The real-time status of the patient may also include vital signs of the patient, clinical device functionality information, or any other relevant patient information that may be monitored. Clinical device functionality information, as previously explained, may indicate whether the clinical device is appropriate for use.

At block 330, based on the patient clinical information and the location status of the patient, is it determined that an alert is required. The alert may be a location-based alert. For example, a patient may be identified as a high risk patient in the patient's EHR such that when the patient is mobile, an alert is required. A patient may be identified as a high-risk patient in their EHR for various reasons including if the patient, e.g., has Alzheimer's disease, is a prisoner, is under a psychiatric hold, is a pediatric patient or an orthopedic patient, or the like. FIG. 5 illustrates a patient that has been identified as a high risk patient that is the subject of an alert generated as a result of the mobility of the patient.

Alerts are not limited to location-based alerts. Other exemplary alerts include an alert indicating that a clinical device requires attention, an alert indicating that a patient has activated a patient call button, or the like. The alerts may be ranked by severity as mild alerts, moderate alerts, severe alerts, and the like, such that clinicians can quickly prioritize displayed alerts.

Upon determining that an alert is required, the alert is presented in both an alert area of a user interface and a blueprint area of the user interface at block 340. The alert is presented in both the alert area and the blueprint area such that the alert is visible while simultaneously viewing the subject of the alert within the blueprint area. Thus, a clinician may easily identify the location of the patient associated with the alert generated and may quickly respond. Such a simultaneous display is illustrated in FIG. 5. In alternative embodiments, a real-time video feed of the patient, wherever the patient location is determined to be, may also be presented on the user interface.

Figure 4:
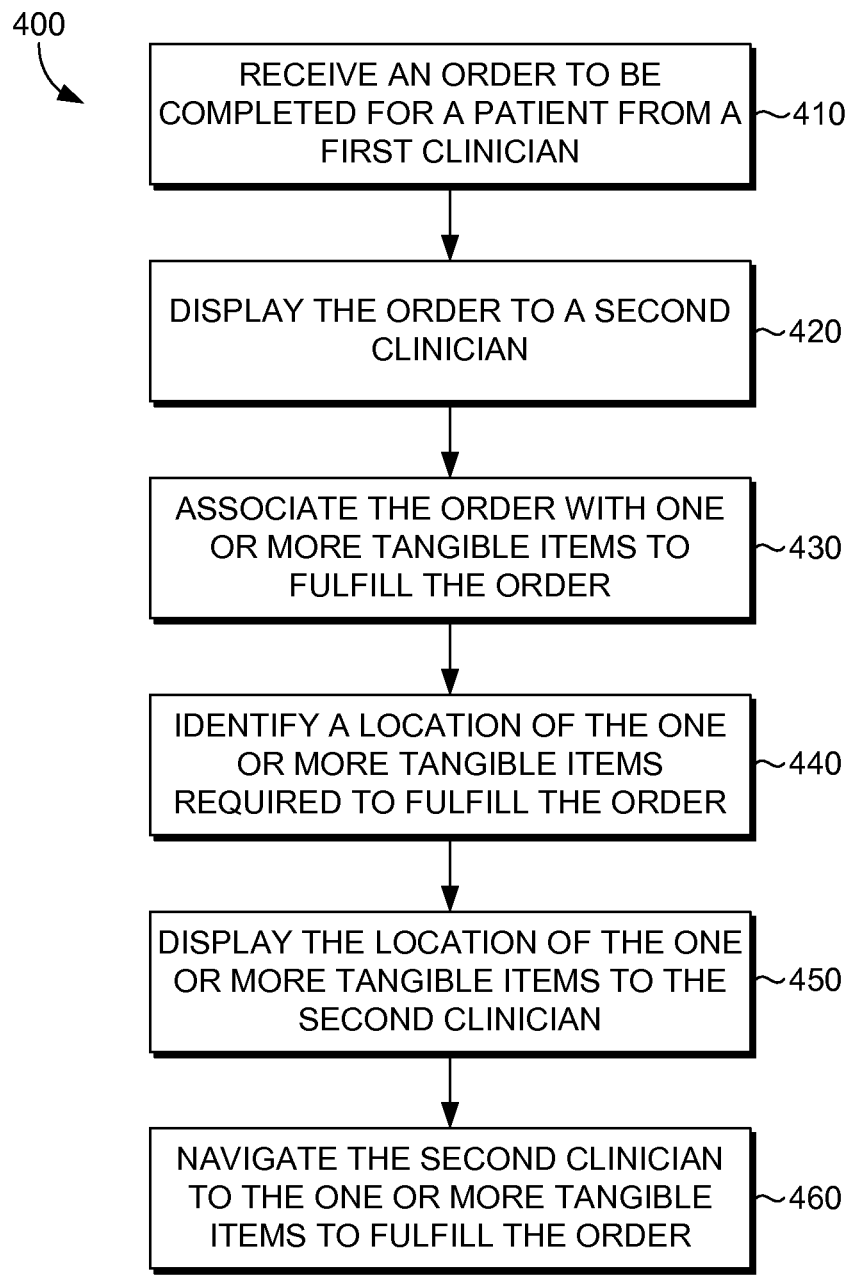
FIG. 4 is a flow diagram illustrating a third exemplary method for managing healthcare environments, in accordance with an embodiment of the present invention.

Turning now to FIG. 4, an exemplary method 400 for managing healthcare environments is illustrated. Initially, a healthcare order to be completed for a patient is received from a first clinician at block 410. The order may be input directly into a patient's EHR. Upon receipt of the healthcare order, the healthcare order is displayed to a second clinician at block 420. The second clinician may be associated with the patient in the patient's EHR, may be a clinician near the location of the patient, or the like. For instance, a general healthcare order for a patient that may be completed by a nurse may be presented to the nurse associated with the patient in the patient's EHR. Alternatively, the healthcare order may be presented to a nurse that is near the patient. Further, the healthcare order may need to be performed by a specific clinician, e.g., a specialist, so the healthcare order may be presented to the specified clinician.

The healthcare order is associated with one or more tangible items to fulfill the healthcare order at block 430. Healthcare orders may require one or more items in order to complete the order. For instance, a healthcare order to administer an IV may require a needle, an IV bag, the ordered fluids, and the like. Once the healthcare order is associated with one or more tangible items, a location of the one or more tangible items is identified at block 440. Similar to the location of patients, clinicians, and clinical devices, the locations of tangible items within a healthcare environment are also monitored via the plurality of sensors within the healthcare environment. The tangible items may be associated with a tag or any other item identifier that may be tracked by the plurality of sensors.

Upon identifying the location of the one or more tangible items required to fulfill the healthcare order, the location of the one or more tangible items is displayed to the second clinician at block 450. The location of the one or more tangible items may be displayed within the blueprint of the healthcare environment, as illustrated in FIG. 5. The second clinician is then navigated to the location of the one or more tangible items via a blueprint of the healthcare facility at block 460. The blueprint may graphically illustrate the location of the clinician and the location of the one or more tangible items. The respective locations are updated as a new sensor identifies the identifier. Thus, as the clinician moves closer to the tangible item, the blueprint updates to illustrate that the clinician's location is changing. Alternatively, turn-by-turn directions may be displayed to the clinician in addition to the graphical blueprint. Thus, a user may be able to view where they are on the blueprint relative to the tangible item and, additionally, view turn-by-turn textual directions simultaneously.

Turning to FIG. 5, a graphical user interface 500 includes a location identification area 530, a blueprint area 510, and a list area 540. Location identification area 530 includes information for a specific location of a healthcare environment such as a floor, wing, etc., of a healthcare facility. For example, in FIG. 5, Level 2 West is the designated location for the current view. Detailed information for Level 2 West is illustrated in location identification area 530 including the number of available beds, the number of beds occupied, a statistical analysis of the bed utilization rate, and the like. An average length of stay may also be displayed in location identification area 530, as well as other information that will be apparent to those of ordinary skill.

When a specific area of a healthcare environment is identified in location identification area 530 (e.g., Level 2 West), blueprint area 510 of user interface 500 presents a blueprint of the identified location. The blueprint of the identified location may be modeled from actual blueprints of the facility. Blueprint area 510 illustrates locations of patient rooms using a patient room icon 512, as well as other areas, and the number and location of beds using a bed icon 513 therein. Blueprint area 510 may designate beds as occupied or non-occupied beds. For example, an occupied bed may include the name of a patient assigned to the bed or, alternatively, an occupied identifier. Bed icon 513 illustrates a non-occupied bed since bed icon 513 indicates that a patient may be added.

Blueprint area 510 may also illustrate the location of patients by way of a patient icon 514, each icon being associated with an individual patient. For example, patient RT, illustrated in FIG. 5 as patient icon 514, is located near the restrooms and, as such, is illustrated in that location on the blueprint 510. Similarly, clinician locations may be illustrated using a clinician icon 515 that is associated with a particular clinician. For example, clinician KR is located in the Nurses Station where clinician icon 515 is displayed. Clinical device locations may also be illustrated within blueprint area 510 with a clinical device icon 518. Clinical device icon 518 illustrates that a clinical device is located in the Nurses Station. Detailed information regarding the patient, the clinician, or the clinical device may be displayed by hovering over the respective icon associated with the patient, clinician, or clinical device.

The icons for patients, clinicians, and clinical devices may be customized such that the icons are easily distinguishable. For example, patients may have an icon that is a certain shape and/or color while clinicians may have an icon that is another shape and/or color. Further clarification may be accomplished by associating specific clinicians with a certain shape and/or color. For instance, a doctor may be associated with one color while a nurse is associated with another color. FIG. 5 distinguishes patients from clinicians by illustrating patient icons 514 with an inverted triangular shape while clinician icons 515 are illustrated as a rectangular shape. Such distinction of icons facilitates quick and easy identification of patients, clinicians, and/or clinical devices within blueprint area 510.

Blueprint area 510 allows a clinician to interact with the information displayed thereon. As previously explained, patient rooms include beds and patients may or may not be assigned to the beds. Bed icon 513 illustrates an empty bed than may have a patient added and associated therewith. Bed 513 may be hovered over such that an enlarged bed icon is displayed. For example, the bed icon for Room 207-A displays detailed bed icon 516 when hovered over. Detailed bed icon 516 identifies a patient assigned to the bed and identifies a current location of the patient. For example, patient Pamela Kohler is assigned to bed 207-A but the current location identifies that the patient is in the hallway. Detailed bed icon 516 includes a patient information icon 519, a clinician information icon 570, a clinical device information icon 571, and an alert icon 574.

Figure 6:
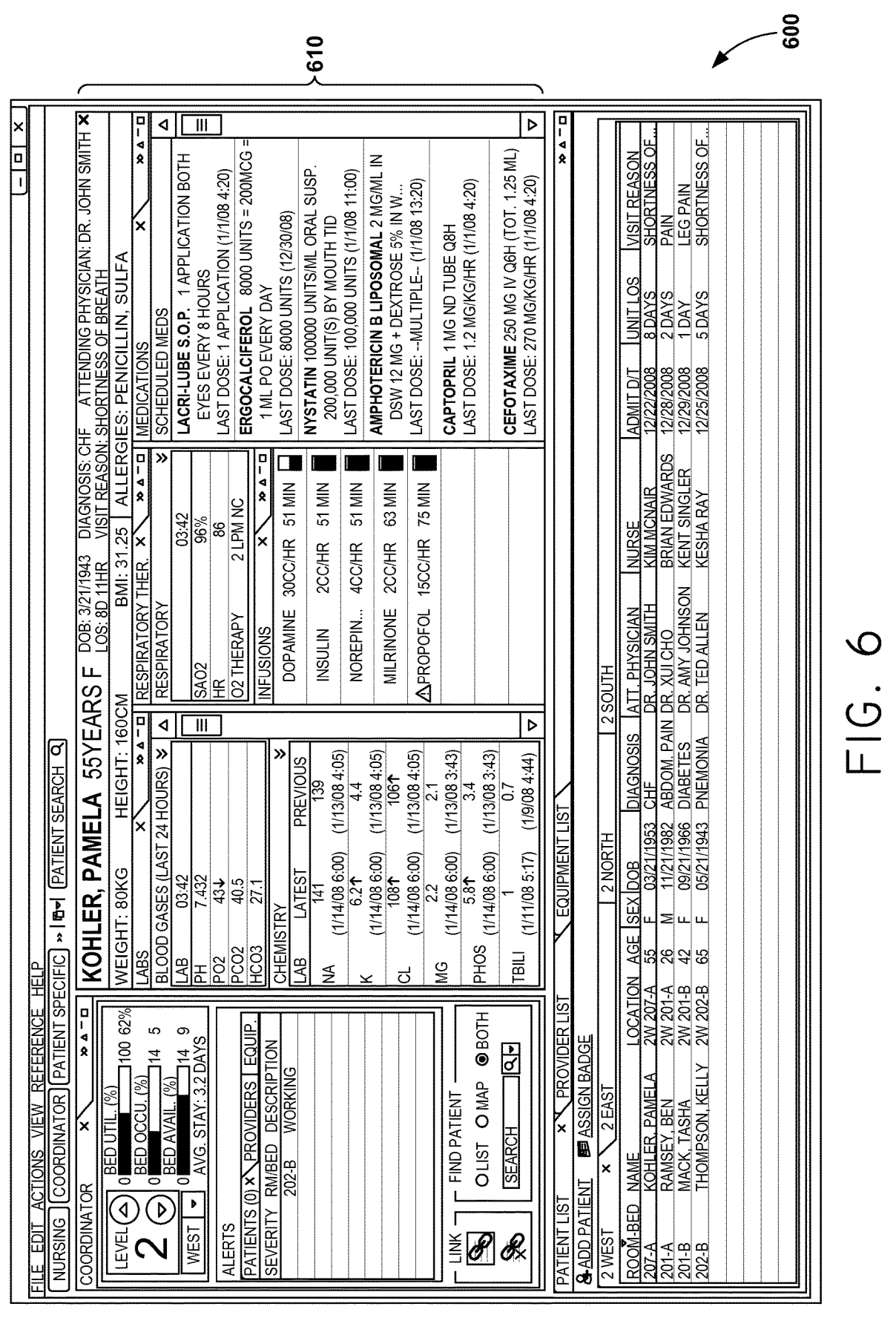

Patient information icon 519 may be hovered over such that detailed patient information is displayed including detailed patient information similar to that illustrated in FIG. 6. Detailed patient information may also be displayed by hovering over patient icon 514.

Figure 7:
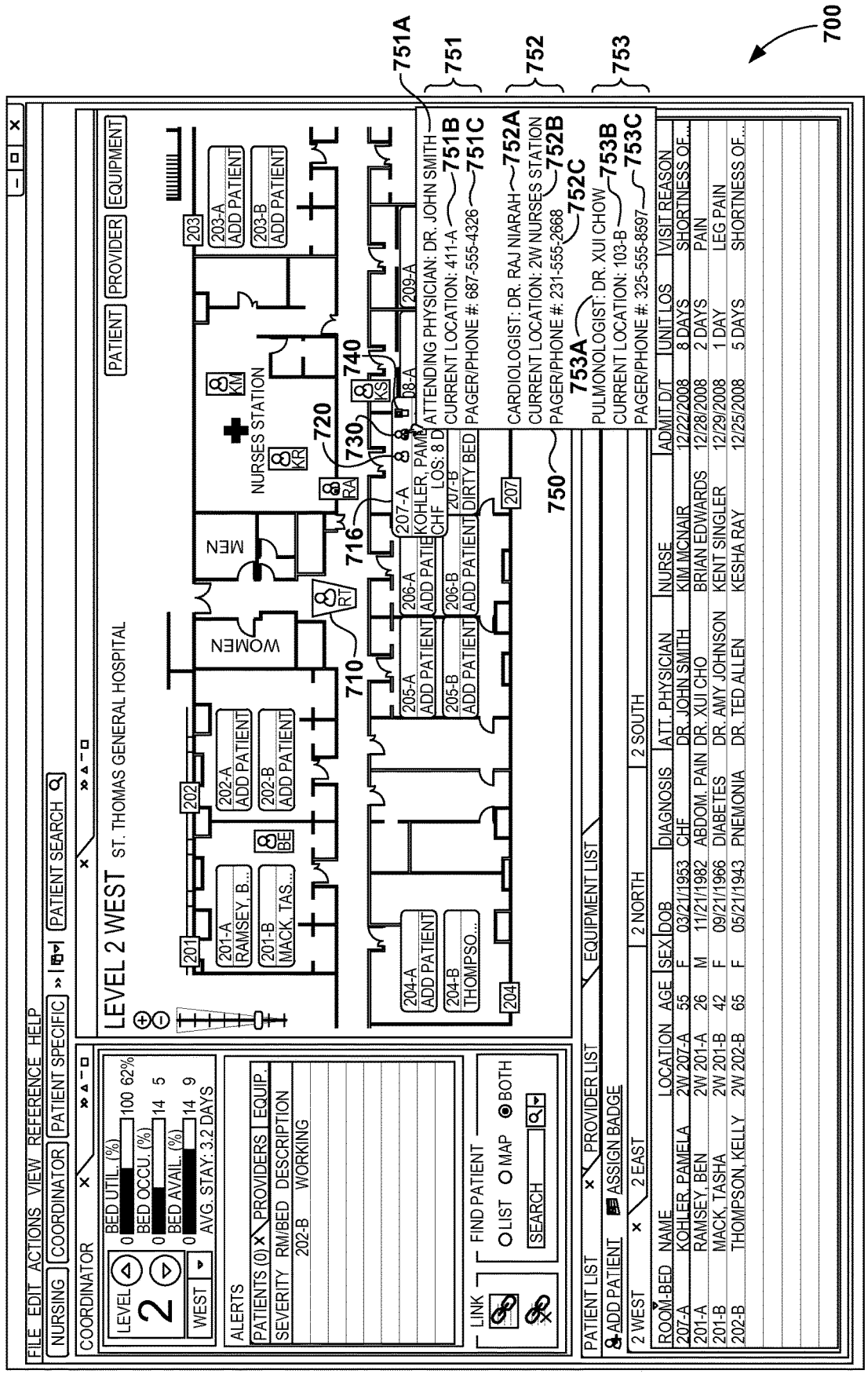
FIG. 7 is an illustrative graphical user interface display of detailed clinician information, in accordance with an embodiment of the present invention.

Clinician information icon 570 may be hovered over such that detailed clinician information associated with the selected patient is displayed. For instance, detailed clinician information for clinicians associated with patient Pamela Kohler is displayed when clinician information icon 570 is hovered over. Said detailed clinician information is illustrated in FIG. 7 and discussed in further detail below.

Figure 9:
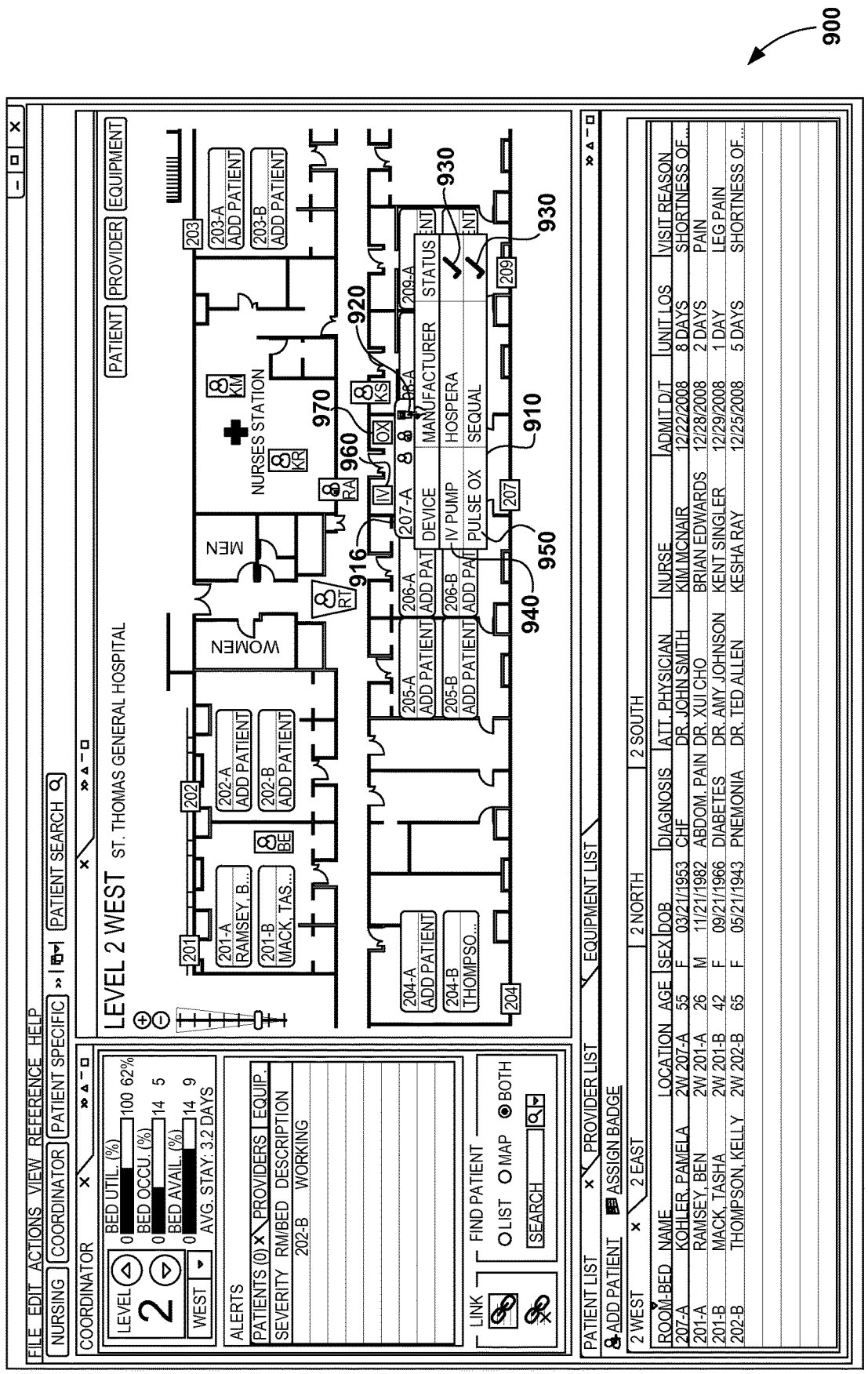
FIG. 9 is an illustrative graphical user interface display of detailed clinical device information, in accordance with an embodiment of the present invention.

Clinical device information icon 571 may also be hovered over such that detailed clinical device information is displayed. The clinical device information, as with the clinician information, is associated with the patient. FIG. 9 illustrates an exemplary display of detailed clinical device information and will be discussed in further detail below.

Alert icon 574 displayed in blueprint area 510 corresponds with an alert icon 521 displayed in an alert area 520. Alert area 520 includes alerts for the location designated in location identification area 530. The alerts, as shown, may be ranked by severity and indicated as mild, moderate, or severe by way of a severe alert icon 521, a moderate alert icon 522, or a mild alert icon 523. Alert area 520 also identifies the location of the alert in addition to a description of the alert.

Upon user selection of alert icon 521 in alert area 520 or by hovering over alert icon 574 within bed icon 516, detailed information regarding the alert is displayed. Alert information balloon 550 is an example of said detailed information. Alert information balloon 550 is illustrated in connection with a selection of alert icon 521 from alert area 520.

Alert information balloon 550 includes detailed information of the alert and of the subject of the alert. A subject identifier 551 may be included in alert information balloon 550 and identifies the subject of the alert by name, age, sex, date of birth, or the like. A diagnosis 552 of the subject of the alert may also be included in alert information balloon 550, as well as a length of stay indicator 553. The information included in alert information balloon 550 may be directly from the patient's EHR.

Additional detailed alert information is also included in alert information balloon 550. A description 554 of the alert is listed. Alert information balloon 550 was generated for a high risk patient who is determined to be off the unit. Blueprint area 510 complements the generated alert by illustrating the location of the subject. For instance, patient Pamela Kohler is determined to be off the unit and blueprint area 510 displays a patient icon 517 for Pamela Kohler in the hallway. The subject of the alert may be highlighted in the blueprint area 510 such that it is quickly located. For example, patient icon 517 may be flashing, highlighted in a bright color, or the like.

A time stamp 555 including a date of the alert and a time of the alert is included in alert information balloon 550. Further, an assigned caregiver 556 is also illustrated such that a notification may be generated to the assigned caregiver. For instance, Nurse Kim McNair is assigned to patient Pamela Kohler in alert information balloon 550 so a notification of the alert may be generated and sent to Nurse Kim McNair. A time elapsed 557 for the alert is also included in the alert information balloon 550 such that caregivers may easily determine how long the alert has been in effect.

As previously discussed, alerts are not limited to patients. An alert may be generated for a clinical device that is not appropriate for use. A warning may be displayed via a pop-up warning, a flashing clinical device icon, upon selection of the alert within alert area 520, or the like. An exemplary clinical device alert is illustrated in alert area 520 by alert 522 indicating that an IV pump is low on fluids. Similar to displaying a subject patient of an alert, a subject clinical device may be displayed within blueprint area 510, as illustrated by IV pump icon 572 illustrating that the IV pump in Room 201-A is low and requires attention.

In additional embodiments, a replacement clinical device may also be presented in blueprint area 510. For example, assume that IV pump icon 572 illustrated that the IV pump is no longer appropriate for use. Replacement IV 573 may be displayed within blueprint area 510 such that a clinician may easily identify a replacement clinical device.

Clinical devices, or any tangible item, may be displayed in blueprint area 510 in response to receiving a healthcare order from a clinician. For example, a healthcare order may be input to get a patient in Room 201-B on an IV pump. A clinician that is associated with the patient may see the alert and need to locate an IV pump. Blueprint area 510 may display a replacement device, e.g., replacement IV pump 573. The replacement device is, thus, easily located by the clinician.

User interface 500 further includes list area 540. List area 540 includes a patient indicator 541, a clinician indicator 542, and an equipment indicator 543. List area 540 may be configured to include a variety of other indicators for various resources found within a healthcare environment.

Patient indicator 541 may be selected to present patient information including a list of patients assigned to the designated location of location identification area 530. The list of patients further includes an assigned room for each patient, a current location for each patient, clinical information, clinicians associated with each patient, reason for the visit to the healthcare facility, the length of stay, and the like. List area 540 also includes selectable tabs for areas of the healthcare facility that are not indicated as the current location in location identification area 530. For example, FIG. 5 illustrates that Level 2 West is currently selected in list area 540 and may be the default location since Level 2 West is the location indicated in location identification area 530. However, there are selectable tabs for each of 2 East, 2 North, and 2 South, such that the patients of other areas of the facility are easily accessible. List area 540 is displayed simultaneously with blueprint 510, alert area 520, and location information area 530.

List area 540 may also present clinician information when clinician indicator 542 is selected. The clinician information may include a clinician's current location, a list of all patients assigned to the clinician and a location of each of the patients, contact information for the clinician, or the like.

Further, list area 540 may also present equipment information when equipment indicator 543 is selected. Similar to the presentation of the patient information, the equipment may also be organized based on location in the healthcare environment. For instance, the default location may be the location that corresponds to that indicated in location identification area 530 while other areas may be accessed upon selection of a new location tab 544 regardless of the location indicated in location identification area 530.

Additional information associated with clinicians, patients, rooms, equipment, or the like, may be accessed through interactive user interface 500. A more detailed view of patient information may be desired and an exemplary user interface 600 is illustrated in FIG. 6. Such a detailed view may be presented upon selection of a patient from the list of patients in list area 540 of FIG. 5. As shown in FIG. 6, patient Pamela Kohler has been selected from the list of patients and a patient summary area 610 presents a detailed view of the patient's clinical information. The information presented in patient summary area 610 may be accessed directly from a patient's EHR and presented on user interface 600.

Turning to FIG. 7, detailed clinician information associated with a patient is displayed. As explained regarding FIG. 5, clinician information icon 730 may be hovered over to access clinician information associated with the patient assigned to the bed. In alternative embodiments, patient icon 720 may be hovered over to retrieve clinician information associated with the patient. With respect to FIG. 7, clinician information icon 730 was hovered over such that clinician information balloon 750 is displayed. A clinician information balloon may include one or more clinicians associated with the indicated patient, a current location for each clinician, as well as contact information, such as a mobile phone or pager number, for the clinician. Effortless identification of associated clinicians and the location thereof facilitates easy communication to relevant clinicians regarding their patients.

Clinician information balloon 750 includes a first clinician information area 751, a second clinician information area 752, and a third clinician information area 753. All three clinicians are related to the patient in some fashion and are included in clinician information balloon 750. First clinician information area 751 includes a first clinician identifier 751a that identifies the first clinician by name and identifies the role of the clinician (e.g., cardiologist, attending physician, etc.). First clinician information area 751 also includes a current location 751b of the clinician. The location of the first clinician is obtained via the plurality of sensors within the healthcare environment, as previously discussed in detail. The first clinician information area 751 further includes first clinician contact information 751c. Contact information may include a mobile phone number, a pager number, an email address, and the like.

Second clinician information area 752 includes a second clinician identifier 752a, a current location 752b of the second clinician, and second clinician contact information area 752c. Similarly, third clinician information area 753 includes a third clinician identifier 753a, a current location 753b of the third clinician, and a third clinician contact information area 753c. The clinician information balloon 751 may include as many clinicians as are associated with a patient.

Figure 8:
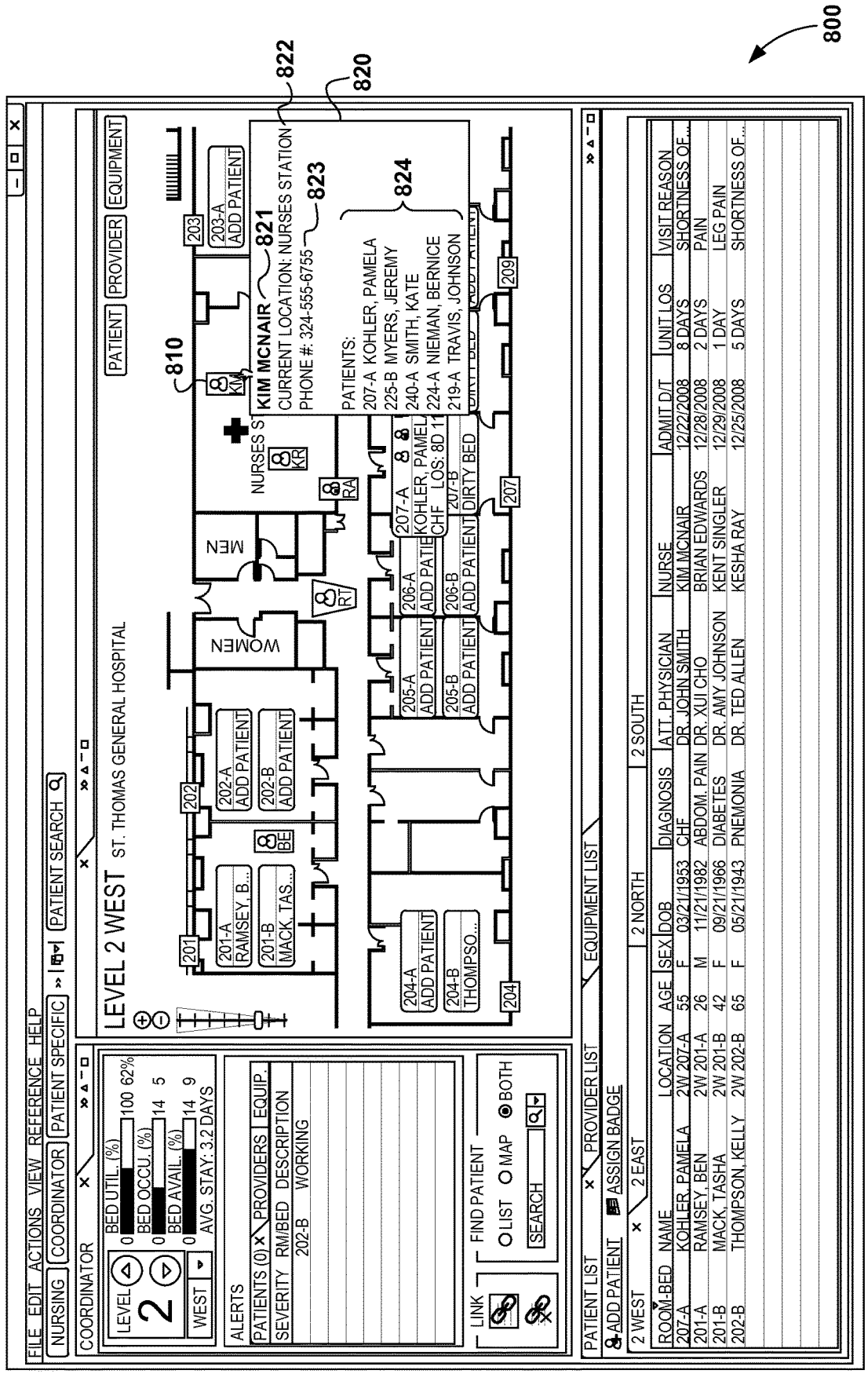
FIG. 8 is an illustrative graphical user interface display of detailed clinician information, in accordance with an embodiment of the present invention.

Turning now to FIG. 8, accessing clinician information is illustrated. Clinician icon 810 may be hovered over such that clinician information balloon 820 is presented. Clinician information balloon 820 may include a clinician identifier 821 that identifies the clinician, a current location 822 for the indicated clinician, and contact information 823 for the clinician. Additionally, a list of patients 824 that are associated with the clinician may be presented in clinician information balloon 820. The list of patients that are associated with the clinician may also include an assigned location for each patient, a current location for each patient, and the like.

In addition to detailed clinician information, detailed information regarding clinical devices may be presented as illustrated by graphical user interface 900 in FIG. 9. Clinical device information balloon 910 is displayed upon receiving an indication that a user is hovering over a clinical device information icon 920. Clinical device information balloon 910 may include a list of all clinical devices associated with the indicated patient and the manufacturer of each listed clinical device. Clinical device information balloon 910 may also include a status indicator 930 for each listed clinical device. For instance, the clinical devices associated with the patient indicated in FIG. 9 are an IV pump 940 and a pulse oxygen device 950, which are graphically illustrated in user interface 900 by IV pump icon 960 and pulse oxygen icon 970. Each is associated with a manufacturer and a status. Status indicator 930 for both the IV pump 940 and the pulse oxygen device 950 indicate that each machine is functioning. The "check-mark" is meant to be illustrative rather than restrictive and any identifier that conveys the status of the clinical device as working may be sufficient in the present invention. Alternatively, status indicator 930 may need to indicate that a clinical device is not working. Said non-functionality may be presented by way of a number of identifiers that would convey that the clinical device is not working.

As previously indicated, the status of a clinical device may contain more information than merely a working or non-working indication. The status may indicate that the device is currently in use or not currently in use. Thus, the device may be in use and working, not in use and working, in use and not working, or not in use and not working.

Figure 10:
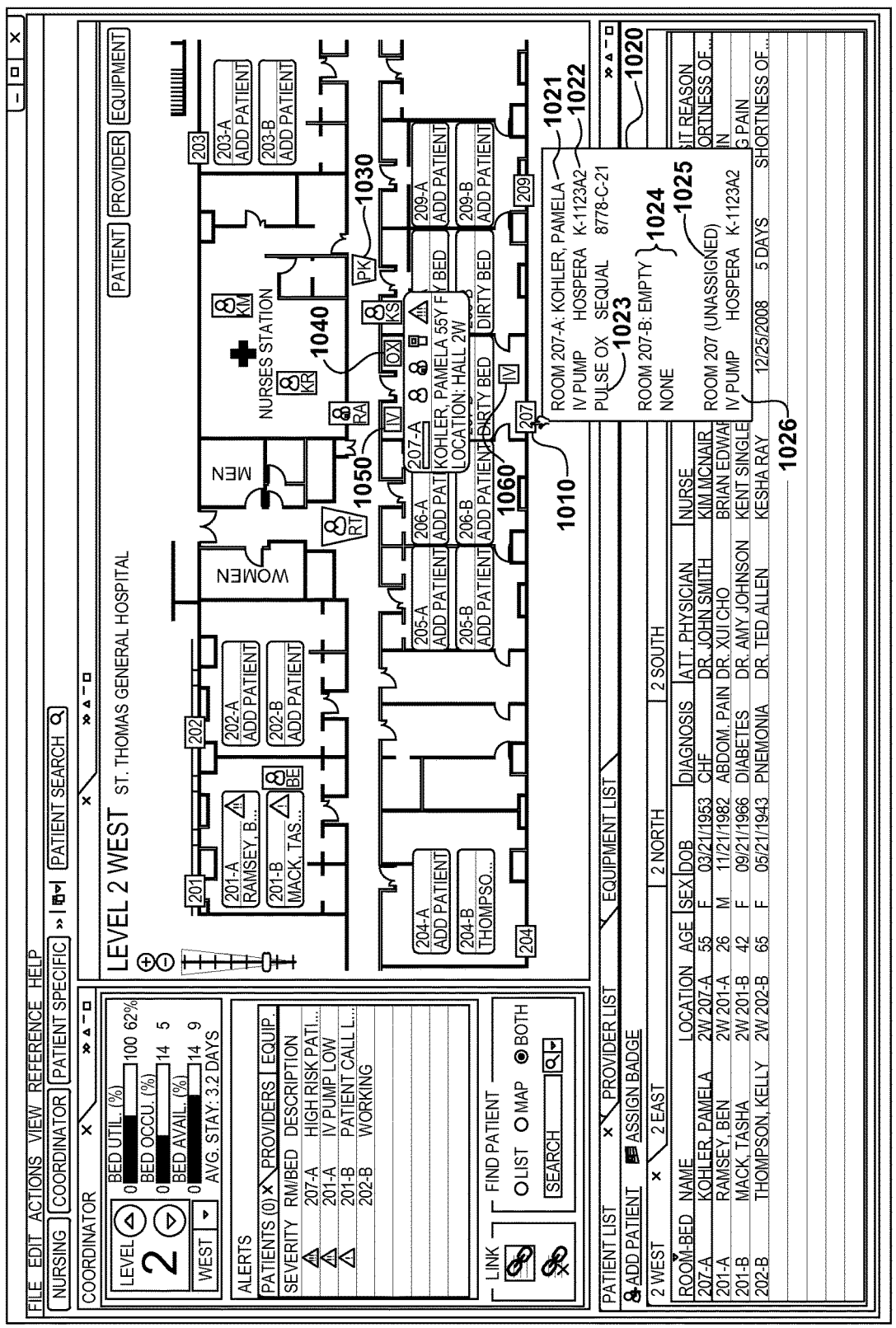
FIG. 10 is an illustrative graphical user interface display of detailed clinical device and patient information accessed in association with a patient room, in accordance with an embodiment of the present invention.

Additional information regarding clinical devices may be accessed, as illustrated by graphical user interface 1000 in FIG. 10. For example, patient room icon 1010 may be hovered over such that a room information balloon 1020 is generated. Room information balloon 1020 may include a list of all patients assigned to the room, as well as a list of all clinical devices assigned to that patient and/or to the room. Room information balloon 1020 may indicate whether the clinical devices assigned to that patient are actually present in the room. Room information balloon 1020 may also indicate clinical devices present in the room that are not assigned to the room or the patient.

As illustrated in FIG. 10, room information balloon 1020 includes an identification of a patient 1021. Additionally, devices 1022 and 1023 are listed such that a user may easily identify the devices assigned to the identified patient 1021. The devices are also displayed within the blueprint by pulse oxygen icon 1040 and IV icon 1050.

Room information balloon 1020 also illustrates an empty room identifier 1024 since the room is not associated with a patient and has no devices. Room information balloon 1020 further illustrates unassigned information 1025 by listing unassigned clinical device 1026. Unassigned clinical device 1026 is also illustrated in the blueprint area by unassigned device icon 1060.

The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects hereinabove set forth together with other advantages which are obvious and which are inherent to the system and method. It will be understood that certain features and subcombinations are of utility and may be employed without reference to other features and subcombinations. This is contemplated by and is within the scope of the claims.

Having thus described the invention, what is claimed is:

1. One or more non-transitory computer-storage media having computer-useable instructions embodied thereon that, when executed, perform an improved method in a medical information computing system of accurately monitoring and managing healthcare environments to identify an alert in signals received from one or more identifiers in a sensor system communicating with a server through a computer network via a plurality of sensors and to generate a graphical user interface to display the alert utilizing location awareness in combination with electronic health records and electronic storage of clinical information the method comprising:

receiving, by the server configured to operate in a healthcare environment, through the computer network, patient clinical information from a patient's electronic health record stored in a database;

the server receiving through the computer network, signals from the one or more identifiers associated with the patient via sensors in the sensor system and identifying from the signals a real-time clinical status of the patient including one or more vital signs of the patient, functionality information of one or more clinical devices associated with the patient, and a real-time location of the patient from the signals, and wherein the functionality information of the one or more clinical devices at least indicates whether the one or more clinical devices are functioning and are appropriate for use;

immediately determining by the server that the alert is necessary based on the patient clinical information from the patient's electronic health record and the identified real-time clinical status of the patient together with the included one or more vital signs of the patient, the functionality information of the one or more clinical devices associated with the patient, and the real-time location of the patient;

upon determining that the alert is necessary, the server generating an alert from the patient clinical information, the identified real-time clinical status of the patient including the one or more vital signs of the patient, the functionality information of the one or more clinical devices associated with the patient, and the real-time location of the patient, the alert including a severity of the alert;

the server generating the graphical user interface automatically without user interaction which displays via a display of a computing device the alert including the identified real-time clinical status of the patient including the real-time location of the patient, and the severity of the alert simultaneously in both an alert area of the graphical user interface and a separate blueprint area of the graphical user interface such that the alert is visible in the alert area simultaneously with a graphical illustration of the real-time location of the patient displayed within the blueprint of the facility in the separate blueprint area of the graphical user interface, wherein a diagnosis and a visit reason are displayed in a list area of the graphical user interface simultaneously with the graphical illustration of the real-time location of the patient displayed within the blueprint of the facility in the separate blueprint area of the graphical user interface and the alert in the alert area of the graphical user interface;

the server receiving an indication of user interaction with the displayed alert; and upon receiving an indication of user interaction with the displayed alert, the server updating the graphical user interface to display via the display of a computing device additional details of the alert in an alert information area on the graphical user interface simultaneously with previously simultaneously but separately displayed diagnosis and visit reason in the list area of the graphical user interface, alert in alert area of the graphical user interface and alert in the separate blueprint area of the graphical user interface, wherein the additional details of the alert includes a determined elapsed time indicating a duration since the alert was generated by the server based on a time of the alert, the identified real-time clinical status of the patient including the one or more vital signs of the patient, the functionality information of the one or more clinical devices associated with the patient as well as patient clinical information and is visible simultaneously with the diagnosis and visit reason in the list area of the graphical user interface, the graphical illustration of the real-time location of the patient displayed within the blueprint of the facility in the separate blueprint area of the graphical user interface, and the alert in the alert area of the graphical user interface.

2. The computer-storage media of claim 1, further comprising:
presenting a live video feed of a patient's room in response to identifying that an alert is in effect for the patient.

3. The computer-storage media of claim 1, wherein the plurality of sensors utilize ultrasound technology, infrared technology, or radio frequency identification technology.

4. The computer-storage media of claim 1, wherein the patient identifier is a patient wristband.

5. A method of accurately monitoring and managing healthcare environments to identify an alert in signals received from one or more identifiers in a sensor system communicating with a server via a plurality of sensors through a computer network and to generate a graphical user interface to display the alert utilizing location awareness in combination with electronic health records and electronic storage of clinical information the method comprising:
the server receiving through the computer network, patient clinical information from a patient's electronic health record stored in a database;
the server receiving through the computer network, signals from the one or more identifiers associated with the patient and the server identifying a real-time clinical status of the patient including one or more vital signs of the patient, functionality information of one or more clinical devices associated with the patient and a real-time location of the patient from the signals, and wherein the functionality information of the one or more clinical devices at least indicates whether the one or more clinical devices are functioning and are appropriate for use;
immediately determining by the server that the alert is necessary based on the patient clinical information from the patient's electronic health record and the real-time clinical status of the patient together with the included the one or more vital signs of the patient, the functionality information of the one or more clinical devices associated with the patient, and the real-time location of the patient identified from the signals;
upon determining that the alert is necessary, the server generating an alert from the patient clinical information and the real-time clinical status of the patient including the one or more vital signs of the patient, the functionality information of the one or more clinical devices associated with the patient, and the real-time location of the patient, the alert including a severity of the alert;
the server generating the graphical user interface automatically without user interaction which displays via a display of a computing device the alert including the real-time clinical status of the patient including the real-time location of the patient received from the one or more identifiers associated with the patient, and the severity of the alert simultaneously in both an alert area of the graphical user interface and a separate blueprint area of the graphical user interface such that the alert is visible in the alert area simultaneously with a graphical illustration of the real-time location of the patient displayed within the blueprint of the facility in the separate blueprint area of the graphical user interface, wherein a diagnosis and a visit reason are displayed in a list area of the graphical user interface simultaneously with the graphical illustration of the real-time location of the patient displayed within the blueprint of the facility in the separate blueprint area of the graphical user interface and the alert in the alert area of the graphical user interface;
the server receiving an indication of user interaction with the displayed alert; and
upon receiving an indication of user interaction with the displayed alert, the server updating the graphical user interface to display via the display of a computing device additional details of the alert in an alert information area on the graphical user interface simultaneously with previously simultaneously but separately displayed diagnosis and visit reason in the list area of the graphical user interface, alert in alert area of the graphical user interface and alert in the separate blueprint area of the graphical user interface, wherein the additional details of the alert includes a determined elapsed time indicating a duration since the alert was generated by the server based on a time of the alert, the real-time clinical status of the patient including the one or more vital signs of the patient, the functionality information of the one or more clinical devices associated with the patient, as well as patient clinical information and is visible simultaneously with the diagnosis and visit reason in the list area of the graphical user interface, the graphical illustration of the real-time location of the patient displayed within the blueprint of the facility in the separate blueprint area of the graphical user interface and the alert in the alert area of the graphical user interface.

6. The method of claim 5, further comprising:
presenting a live video feed of a patient's room in response to identifying that an alert is in effect for the patient.

7. The method of claim 5, wherein the plurality of sensors utilize ultrasound technology, infrared technology, or radio frequency identification technology.

8. The method of claim 5, wherein the patient identifier is a patient wristband.

9. A computing system comprising:
one or more processors;
one or more databases;
one or more output devices; and
computer storage memory having computer-executable instructions stored thereon which for accurately monitoring and managing healthcare environments to identify an alert in signals received from one or more identifiers in a sensor system communicating via a plurality of sensors through a computer network with a server and to generate a graphical user interface displaying the alert utilizing location awareness in combination with electronic health records and electronic storage of clinical information, when executed by at least one processor, configure the computer system to:
receive by the one or more processors patient clinical information from a patient's electronic health record stored in a database;
receive by the one or more processors signals from the one or more identifiers associated with the patient and identify a real-time clinical status of the patient including the one or more vital signs of the patient, the functionality information of the one or more clinical devices associated with the patient, and a real-time location of the patient from the signals, and wherein the functionality information of the one or more clinical devices at least indicates whether the one or more clinical devices are functioning and are appropriate for use;
immediately determine by the one or more processors that the alert is necessary based on the patient clinical information from the patient's electronic health record and the real-time clinical status of the patient together with the included the one or more vital signs of the patient, the functionality information of the one or more clinical devices associated with the patient, and the real-time location of the patient received from the plurality of sensors in the sensor system;

upon determining that the alert is necessary, generate by the one or more processors the alert from the patient clinical information and the real-time clinical status of the patient including the one or more vital signs of the patient, the functionality information of the one or more clinical devices associated with the patient, and the real-time location of the patient, the alert including a severity of the alert;

generate by the one or more processors a graphical user interface automatically without user interaction which displays via at least one of the one or more output devices the alert simultaneously in both an alert area of the graphical user interface and a separate blueprint area of the graphical user interface such that the alert is visible in the alert area simultaneously with a graphical illustration of the real-time location of the patient received from the one or more identifiers associated with the patient displayed within the blueprint of the facility in the separate blueprint area of the graphical user interface, wherein a diagnosis and a visit reason are displayed in a list area of the graphical user interface simultaneously with the graphical illustration of the real-time location of the patient displayed within the blueprint of the facility in the separate blueprint area of the graphical user interface and the alert in the alert area of the graphical user interface;

receive an indication of user interaction with the displayed alert; and upon receiving an indication of user interaction with the displayed alert, update the graphical user interface to display via at least one of the one or more output devices additional details of the alert in an alert information area on the graphical user interface simultaneously with previously simultaneously but separately displayed diagnosis and visit reason in the list area of the graphical user interface, alert in alert area of the graphical user interface and alert in the separate blueprint area of the graphical user interface, wherein the additional details of the alert includes a determined elapsed time indicating a duration since the alert was generated by the server based on a time of the alert, the real-time clinical status of the patient including the one or more vital signs of the patient, the functionality information of the one or more clinical devices associated with the patient as well as patient clinical information and is visible simultaneously with the diagnosis and visit reason in the list area of the graphical user interface, the graphical illustration of the real-time location of the patient displayed within the blueprint of the facility in the separate blueprint area of the graphical user interface and the alert in the alert area of the graphical user interface.

10. The system of claim 9, further configured to:
present a live video feed of a patient's room in response to identifying that an alert is in effect for the patient.

11. The system of claim 9, wherein the plurality of sensors utilize ultrasound technology, infrared technology, or radio frequency identification technology.

12. The system of claim 9, wherein the real-time clinical status of the patient further includes vital signs of the patient.

13. The system of claim 9, wherein the patient identifier is a patient wristband.

* * * * *